United States Patent
Sargent et al.

[11] Patent Number: 5,877,175
[45] Date of Patent: Mar. 2, 1999

[54] PHARMACEUTICAL COMPOSITIONS

[75] Inventors: Bruce Jeremy Sargent; David John Heal, both of Nottingham, Great Britain; Maria Isabel Fernández Fernández, Madrid, Spain

[73] Assignee: KNOLL Aktiengesellschaft, Ludwigshafen, Germany

[21] Appl. No.: 913,843

[22] PCT Filed: Mar. 26, 1996

[86] PCT No.: PCT/EP96/01318

§ 371 Date: Sep. 23, 1997

§ 102(e) Date: Sep. 23, 1997

[87] PCT Pub. No.: WO96/30364

PCT Pub. Date: Oct. 3, 1996

[30] Foreign Application Priority Data

Mar. 29, 1995 [GB] United Kingdom .................. 9506382

[51] Int. Cl.$^6$ ..................... C07D 403/04; A61K 31/505
[52] U.S. Cl. ........................................... 514/252; 544/238
[58] Field of Search ............... 514/252; 544/238

[56] References Cited

FOREIGN PATENT DOCUMENTS

94/11360  5/1994  WIPO .
95/10521  4/1995  WIPO .

OTHER PUBLICATIONS

Ann. Chem. 58 (1968) pp. 128–135.
Plescia et al., J. Het. Chem. 18 (1981) pp. 333–334.

Primary Examiner—Mukund J. Shah
Assistant Examiner—Deepak Rao
Attorney, Agent, or Firm—Keil & Weinkauf

[57] ABSTRACT

Certain 3-(Pyrimidin-4-yl)-1-phenylpyridazin-4(1H)-ones of formula I

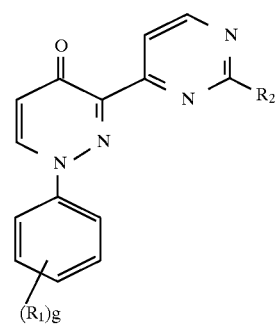

including pharmaceutically acceptable salts thereof; in which g is 0,1,2,3,4 or 5;

$R_1$ independently represents halo; and $R_2$ represents H, $C_{1-4}$ alkyl, $C_{3-6}$ cycloalkyl or optionally substituted phenyl;

have utility in the treatment of seizures and/or neurological disorders such as epilepsy and/or conditions in which there is neurological damage such as brain trauma, cerebral ischaemia, haemorrhage, head injuries and stroke.

7 Claims, No Drawings

PHARMACEUTICAL COMPOSITIONS

This invention relates to certain 3-(pyrimidin-4-yl)-1-phenylpyridazin-4(1H)-ones, to pharmaceutical compositions containing them, to processes for their preparation and to their use in the treatment, prophylaxis and/or inhibition of seizures, neurological disorders such as epilepsy and/or conditions in which there is neurological damage such as brain trauma, cerebral ischaemia, haemorrhage, head injuries and stroke.

In particular the present invention provides compounds of formula I

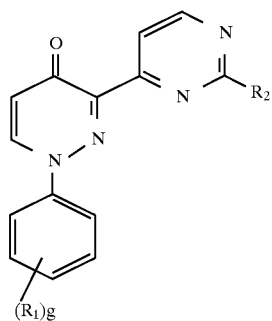

including pharmaceutically acceptable salts thereof; in which g is 0,1,2,3,4 or 5;

$R_1$ independently represents halo; and $R_2$ represents H, $C_{1-4}$ alkyl, $C_{3-6}$ cycloalkyl or phenyl optionally substituted by one or more substituents selected from halo, $C_{1-4}$ alkyl and $C_{1-4}$ alkoxy;

which have utility in the treatment, prophylaxis and/or inhibition of seizures and/or neurological disorders such as epilepsy and/or conditions in which there is neurological damage such as brain trauma, cerebral ischaemia, haemorrhage, head injuries and stroke.

The compound of formula I in which g is 1, $R_1$ is 4-fluoro and $R_2$ is tert-butyl, namely 3-(2-tert-butylpyrimidin-4-yl)-1-(4-fluorophenyl)pyridazin-4(1H)-one, is a commercially available compound. No pharmacological activity has been disclosed for this compound and in addition there have been no disclosures of pharmaceutical compositions containing this compound.

Therefore the present invention provides novel compounds of formula I represented by formula II

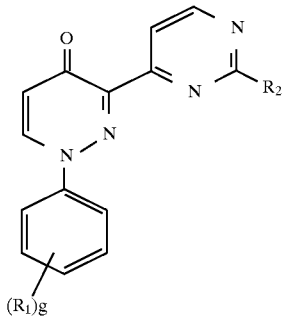

including pharmaceutically acceptable salts thereof; in which g is 0,1,2,3,4 or 5;

$R_1$ independently represents halo; and $R_2$ represents H, $C_{1-4}$ alkyl, $C_{3-6}$ cycloalkyl or phenyl; with the proviso that when g is 1 and $R_1$ is 4-fluoro, then $R_2$ is other than tert-butyl.

Specific compounds of formula I include:
3-(2-tert-butylpyrimidin-4-yl)-1-(4-fluorophenyl) pyridazin-4(1H)-one;
3-(2-isopropylpyrimidin-4-yl)-1-(4-fluorophenyl) pyridazin-4(1H)-one;
3-(2-phenylpyrimidin-4-yl)-1-(4-fluorophenyl)pyridazin-4(1H)-one;
3-(pyrimidin-4-yl)-1-(2,4-dichlorophenyl)pyridazin-4(1H)-one;
3-(2-isopropylpyrimidin-4-yl)-1-(4-chlorophenyl) pyridazin-4(1H)-one;
3-(2-cyclopropylpyrimidin-4-yl)-1 -(4-chlorophenyl) pyridazin-4(1H)-one;
3-(2-cyclohexylpyrimidin-4-yl)-1-(4-fluorophenyl) pyridazin-4(1H)-one;
3-(2-cyclohexylpyrimidin-4-yl)-1-(4-chlorophenyl) pyridazin-4(1H)-one;
3-(2-propylpyrimidin-4-yl)-1-(4-fluorophenyl)pyridazin-4(1H)-one;
including pharmaceutically acceptable salts thereof.

Specific compounds of formula II include:
3-(2-isopropylpyrimidin-4-yl)-1-(4-fluorophenyl) pyridazin-4(1H)-one;
3-(2-phenylpyrimidin-4-yl)-1-(4-fluorophenyl)pyridazin-4(1H)-one;
3- (pyrimidin-4-yl)-1-(2,4-dichlorophenyl)pyridazin-4 (1H)-one;
3-(2-isopropylpyrimidin-4-yl)-1-(4-chlorophenyl) pyridazin-4(1H)-one;
3-(2-cyclopropylpyrimidin-4-yl)-1-(4-chlorophenyl) pyridazin-4(1H)-one;
1- (2-cyclohexylpyrimidin-4-yl)-1-(4-fluorophenyl) pyridazin-4(1H)-one;
3-(2-cyclohexylpyrimidin-4-yl)-1-(4-chlorophenyl) pyridazin-4(1H)-one;
3-(2-propylpyrimidin-4-yl)-1-(4-fluorophenyl)pyridazin-4(1H)-one;
including pharmaceutically acceptable salts thereof.

It will be understood that any group mentioned herein containing a chain of three or more carbon atoms signifies a group in which the chain may be straight or branched. For example, an alkyl group may comprise propyl which includes n-propyl and isopropyl, and butyl which includes n-butyl, sec-butyl, isobutyl and tert-butyl. The total number of carbon atoms is specified herein for certain substituents, for example $C_{1-4}$ alkyl signifies an alkyl group having from 1 to 4 carbon atoms. The term "halo" as used herein signifies fluoro, chloro, bromo and iodo. It will be appreciated that when g is 2,3,4 or 5 then $R_1$ can represent the same halo atom or different halo atoms. It will also be understood that certain compounds of formula I or II, for example when $R_2$ represents sec-butyl, may contain a chiral centre, and exist in different optically active forms. The present invention includes both enantiomers and mixtures of the enantiomers.

The present invention includes all salts of compounds of formula I and II which are pharmaceutically acceptable. Compounds of formula I and II may form salts with organic or inorganic acids (for example acid addition salts). Particularly suitable salts of the present invention comprise salts of acidic amino acids or suitable derivatives thereof (for example salts of glutamic acids and/or N-carbamoyl-phenylalanine), salts of suitable inorganic acids (for example salts of hydrobromic, hydrochloric, hydriodic, nitric, phosphoric, sulphonic or sulphuric acids) or salts of suitable organic acids (for example salts of acetic, alkylsulphonic, alkylsulphuric, arylsulphonic, arylsulphuric, ascorbic, benzoic, cinnamic, citric, dibenozyltartaric, dodecanoic, fumaric, gluconic, glycolic, lactic, maleic, malic, mandelic, palmitic, palmoic, pyruvic, salicylic, succinic or tartaric acids or suitable derivatives thereof). Salts include all pharmaceutically acceptable salts that may be formed from multivalent acids (for example acid metal [such as bicarbonate and/or hydrogen orthphosphate salts]) and all enantiomeric salts formed with pharmaceutically acceptable chiral acids or any mixtures of enantiomers of such salts (for example (+) tartrates and/or (−) tartrates). The above salts may be prepared by reacting a compound of formula I or II with suitable acids in a conventional manner.

Compounds of formula I and II and salts thereof may exist as solvates (for example if the solvent is water the hydrates may be hemihydrates, monohydrates and/or dihydrates) or as an unsolvated form (for example an anhydrous form). The degree of solvation may also be non-stoichiometric. The present invention includes all pharmaceutically acceptable solvates and any mixtures thereof.

Compounds of formula I or II may exist in more than one crystal form. The present invention includes each crystal form and mixtures thereof.

The present invention provides pharmaceutical compositions comprising compounds of formula I including pharmaceutically acceptable salts thereof in conjunction with a pharmaceutically acceptable diluent or carrier.

As used herein, the term "pharmaceutical composition" denotes a pharmaceutical composition comprising a therapeutically and/or prophylactically effective amount of a compound of formula I in conjunction with any pharmaceutically acceptable diluent or carrier.

Pharmaceutical compositions may be prepared by any method known to those skilled in the art, for example by bringing the compound of formula I, hereinafter referred to as the active compound, into association with suitable inert diluents, carriers and/or any other optional ingredients (for example those described herein). The ingredients of the pharmaceutical composition may be intimately admixed and the resultant pharmaceutical composition may be shaped (for example by compressing and/or moulding). It will be appreciated by those skilled in the art that if the pharmaceutical composition contains large amounts of excipients in relation to the active compound, repeated conventional mixing operations may be required to distribute the active compound homogenously throughout the pharmaceutical composition. Pharmaceutical compositions may also be formulated in a manner known to those skilled in the art, to give a modified release (for example rapid, delayed, sustained or controlled release) of the active compound. Pharmaceutically acceptable diluents or carriers suitable for use in pharmaceutical compositions are well known in the art of pharmacy. The excipients used in the preparation of pharmaceutical compositions are the excipients known in the pharmacist's art.

Pharmaceutical compositions may be administered orally in known pharmaceutical forms for such administration which may be solid or fluid. Dosage forms suitable for oral administration may comprise cachets, caplets, capsules, dragees, elixirs, extrudates, granules, lozenges, pastilles, pills, pellets, powders, solutions, suspensions, syrups, tablets and/or troches. Pharmaceutical compositions which are suitable for oral administration are particularly advantageous.

Solid oral dosage forms may be prepared by mixing the active compound with one or more of the following ingredients which are pharmaceutically acceptable: inert diluents, disintegrating agents, lubricants, binders and or any mixtures thereof. It will be appreciated by those skilled in the art that a particular ingredient may perform more than one function (for example maize starch may act as a diluent, binder and/or as a disintegrating agent).

Inert diluents may comprise sugars (for example lactose, fructose, sucrose, powdered sugar and/or mixtures thereof), sugar alcohols (for example mannitol), celluloses (for example microcrystalline cellulose), starches (for example maize starch, other pharmaceutical grade starch or mixtures thereof), dextrin, clays (for example kaolin), inorganic material (for example calcium phosphate, calcium sulphate and/or sodium chloride) and/or mixtures thereof.

Disintegrating agents may comprise starches (for example maize starch, sodium starch glycolate or mixtures thereof), agar, bentonite, celluloses (for example methyl cellulose, carboxymethylcellulose, microcrystalline cellulose, hydroxypropyl cellulose and/or mixtures thereof), alginic acid, alginate salts, guar gum, croscarmellose sodium, sodium lauryl sulphate, colloidal silicon dioxide or mixtures thereof.

Lubricating agents may comprise stearic acid, stearates (for example magnesium stearate, calcium stearate or glyceryl palmitostearate), talc, polyethylene glycol, glyceryl behenate or mixtures thereof.

Binders may comprise starches (for example maize starch), gelatin, sugars (for example sucrose, molasses, lactose and/or mixtures thereof) and/or natural and/or synthetic gums (for example acacia, sodium alginate, celluloses, [such as carboxy methylcellulose, hydroxy propyl methylcellulose, methylcellulose, ethylcellulose, polyethylene glycol, waxes, micro-crystalline cellulose and/or mixing thereof] polyvinylpyrrolidone and/or mixtures thereof).

Solid oral dosage forms of the present invention may further comprise one or more of the following ingredients and/or mixtures thereof:

colouring agents (for example conventional pharmaceutically acceptable and/or food desirable dyes and/or colourants);

sweetening agents (for example intense sweeteners[such as aspartame and/or saccherin]);

flavouring agents (for example pharmaceutically acceptable and/or food desirable flavours);

anti-microbial agents (for example methyl p-hydroxybenzoate, propyl p-hydroxybenzoate, sodium benzoate, sodium propionate and/or sorbic acid);

anti-oxidants (for example ascorbic acid, sodium ascorbate, sodium metabisulphite and/or propyl gallate);

wetting agents (for example sodium lauryl sulphate); and/or one or more pharmaceutically acceptable couples (for example those comprising an acid and a carbonate and/or bicarbonate salt), which effervesce to aid dissolution if the solid dosage form is added to water.

Solid dosage forms of the present invention may also optionally comprise one or more other pharmaceutically acceptable ingredients and/or mixtures thereof, which are known in the art to permit production of oral dosage forms by known methods (for example blending, filling and/or tabletting). Such ingredients may comprise:

agents to aid the flow of ingredients (for example talc and/or colloidal silicon dioxide);

compression agents to increase the strength of the solid dosage form (for example sorbitol and/or lactose); and/or ionic and/or non-ionic surface active agents (for example sodium lauryl sulphate) to disperse the active compound within the solid dosage form and prevent grit forming at the surface of the solid dosage form. Preferably solid oral dosage forms are shaped to be more convenient for general use.

Solid oral dosage forms may be formulated in a manner known to those skilled in the art so as to give a sustained release of the active compound, for example by formulating the active compound with a sustained release excipient for example xanthan gum. Various materials, for example shellac and/or sugar, may be present as coatings, or to otherwise modify the physical form of the oral dosage form. Oral dosage forms may also be film coated for example with hydroxypropylmethyl-cellulose. Enteric coated, solid oral dosage forms comprising pharmaceutical compositions may be advantageous, depending on the nature of the active compound. For example tablets and/or pills may, if desired, be provided with enteric coatings (such as membranes) by known methods, for example by the use of cellulose acetate phthalate, polyvinylacetate phthalate, hydroxypropylmethylcellulose phthalate and/or anionic polymers of methacrylic acid and/or its esters. To prevent and/or reduce cracking of the enteric coating during its application and/or storage of the solid dosage form, the enteric coating may comprise a plasticiser (for example diethyl phthalate, tributyl citrate and/or triacetin).

Capsules (for example hard or soft gelatin capsules) comprising the active compound (with or without added excipients), may be prepared by conventional means and, if desired, provided with enteric coatings in a known manner. The contents of capsules may be formulated using known methods to give sustained release of the active compound.

Tablets and capsules are preferred solid dosage forms. Tablets and capsules may conveniently each contain 0.1 to 1000 mg (for example 10 mg, 50 mg, 100 mg, 200 mg, 400 mg, 600 mg or 800 mg) of the active compound.

The active compound may be formulated into granules and/or powders with or without additional excipients. The granules and/or powders may be ingested directly by the patient or they may be added to a suitable liquid carrier (for example water) before ingestion. The granules and/or powders may contain disintegrants (for example pharmaceutically acceptable effervescent couples formed from acids and carbonate and/or bicarbonate salts) to facilitate dispersion in liquid media.

Fluid oral dosage forms comprising the pharmaceutical compositions are preferably liquid oral dosage forms and may be elixirs, solutions, syrups and/or suspensions which contain the active compound in pharmaceutically acceptable media. Pharmaceutically acceptable solvents comprise water, oils and/or alcohols. Media suitable for preparing syrups and/or suspensions may comprise aqueous media, oily media and/or emulsions in the presence of one or more pharmaceutically acceptable suspending agents (for example starches, gums[such as xanthangum]) celluloses, [such as methylcellulose, hydroxyethyl-cellulose and/or sodium carboxymethylcellulose], gelatin, glycerin, hydrogenated fats and/or sorbitol). Suitable oily media may comprise vegetable oils (for example arachis oil and/or sunflower oil), other edible oils (for example almond oil and/or fractionated coconut oil) and/or oily esters (for example esters of glycerin, propylene glycol and/or ethanol). Fluid oral dosage forms may further comprise one or more of the following which are pharmaceutically acceptable: agents which vary osmotic pressure (for example salts), colouring agents, emulsifiers (for example lecithin, sorbitan monooleate and/or acacia), flavouring agents, pH adjusting agents (for example buffers), preservatives, sweetening agents and/or mixtures thereof. Fluid oral dosage forms may also be prepared from dry products (for example granules and/or powders) which are presented for reconstitution with a suitable vehicle (for example those media described above).

Pharmaceutical compositions may be administered rectally in the known pharmaceutical forms for such administration (for example suppositories with a base comprising sugars, starches, stearates, hard fats, semi-synthetic glycerides, cocoa butter, polyethylene glycols and/or any mixtures thereof).

Pharmaceutical compositions may also be administered parenterally (for example subcutaneously, intramuscularly, intradermally and/or intravenously[such as by injection and/or infusion ])in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents[such as ethylene oxide]). Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

The active compound may also be administered by continuous infusion either from an external source (for example by intravenous infusion) and/or from a source of the active compound placed within the body. Internal sources include implants and/or implanted reservoirs containing the active compound to be infused from which the active compound is continuously released (for example by osmosis). Liquid implants may comprise suspensions and/or solutions in a pharmaceutically acceptable solvent of the active compound to be infused (for example as oily solutions of oils of very sparingly water-soluble derivatives of the active compound such as dodecanoate salts). Solid implants may be in the form of an implanted support (for example synthetic resins and/or waxy materials) for the active compound to be infused. The support may be a single body containing all the active compound or a series of several bodies each containing part of the active compound to be delivered. The amount of active compound present in an internal source should be such that a therapeutically and/or prophylactically effective amount of the active compound is delivered over a long period of time.

The active compound may be suitable for use in so-called depot formulations which provide a source of the active compound located within the body (for example by intramuscular injection). Depot formulations may comprise the active compound in a pharmaceutically acceptable oil.

In some formulations it may be beneficial to use the active compound and/or the pharmaceutical composition in the form of particles of very small size, for example as obtained by fluid energy milling. Alternatively the active compound may be bound (for example by sorption, incorporation and/or chemically) to nanoparticles which are colloidal polymeric particles of a size typically less than 1 micron. The distribution of such nanoparticles in the body and hence the sites of delivery of the active compound can be effected by coating the surface of the nanoparticles appropriately (for example with surfactants and/or antibodies).

In the pharmaceutical composition the active compound may, if desired, be associated with other compatible, pharmacologically active ingredients.

The most suitable route for administering the active compound depends on many factors (for example the particular clinical condition treated, its severity and/or the specific compound used). Preferably, in the treatments described herein, the active compound may be administered orally, rectally, parenterally, nasally, bucally and/or topically; more preferably orally. Thus pharmaceutical compositions suitable for use in the present invention may take the form of any pharmaceutical compositions suitable for such methods of administration (for example one or more of the pharmaceutical compositions described herein and/or any mixtures thereof).

Compounds of formula I including pharmaceutically acceptable salts thereof, and pharmaceutical compositions comprising compounds of formula I, including pharmaceutically acceptable salts thereof, in conjunction with a pharmaceutically acceptable diluent or carrier are indicated for therapeutic use as medicaments, particularly as medicaments for the treatment, prophylaxis and/or inhibition in mammals of seizures, neurological disorders and/or conditions in which there is neurological damage. Specific clinical conditions for which the active compound and/or its pharmaceutical compositions are indicated comprise brain trauma, cerebral ischaemia, epilepsy, haemorrhage, head injuries and stroke.

The therapeutic and/or prophylactic activity of compounds of formula I has been demonstrated by means of various pharmacological tests such as in vitro tests and in vivo tests in standard laboratory animals. Such tests include the test of pharmacological activity described herein.

Therefore the present invention provides a method of treatment, prophylaxis and/or inhibition of seizures, neurological disorders such as epilepsy and/or conditions in which there is neurological damage such as brain trauma, cerebral ischaemia, haemorrhage, head injuries and stroke, which comprises the administration of a therapeutically and/or prophylactically effective amount of a compound of formula I, including pharmaceutically acceptable salts thereof, to a mammal in need thereof. Preferably the mammal is a human being.

It will be appreciated that the term 'therapy' as used herein includes both treatment and/or prophylactic use of the active compound and pharmaceutical compositions comprising a therapeutically effective amount of the active compound. The active compound and/or the pharmaceutical composition may be used to provide a systemic therapeutic and/or prophylactic effect. In the present invention prophylactic use of the active compound comprises administering to an animal in need thereof the active compound to prevent the onset of one or more clinical conditions selected from: seizures, neurological disorders and conditions in which there is neurological damage; and use of the active compound as a neuroprotective agent to protect an animal against one or more clinical conditions selected from: seizures, neurological disorders and conditions in which there is neurological damage.

While the precise mechanism of action of the active compound is unknown at present, it is believed that at least some of the pharmacological effects of the active compound in the clinical conditions described herein may arise from activity blocking one or more voltage-dependent sodium ion (Na+) channels in neurones, potentiating the transmission of the neurotransmitter gamma-amino butyric acid (GABA), attenuating the transmission of the excitatory amino acids (for example glutamic and/or aspartic) and activating one or more potassium ion (K+) and/or calcium ion ($Ca^{2+}$) and/or chloride ion (Cl) channels in neurones. However, the method of treatment of the present invention should not be considered limited to administering pharmaceutical compositions having such pharmacological activity.

The precise amount of the active compound administered to a particular mammal, preferably a human being, in the method of treatment of the present invention will depend on a number of factors (for example: the specific compound administered, its mode of administration and/or the use for which it is intended; the particular clinical condition being treated and/or its severity; and/or the age, body mass and/or past clinical history of the patient to be treated) and always lies within the sound discretion of the person administering and/or supervising the treatment (for example a medical practitioner[such as nurse and/or physician]. Nevertheless, a suitable daily dose of the active compound for administration to an mammal is generally from about 0.01 mg/day per kg of the mammal's body mass to about 80 mg/kg/day, more usually 0.2–40 mg/kg/day given in a single dose and/or in divided doses at one or more times during the day. The total dose of the active compound administered per day may be generally from about 0.1 mg to about 3000 mg, more usually from about 10 to about 1500 mg. The pharmaceutical composition may contain from about 0.1% to about 99% by weight of the active compound and is generally prepared in unit dose form, a unit dose of active compound generally being from about 0.1 mg to about 500 mg. If the active compound is a salt the masses indicated above refer to the mass of the corresponding active compound that is other than a salt.

A further aspect of the present invention provides the use of compounds of formula I or a pharmaceutical composition containing a compound of formula I in the manufacture of a medicament for the treatment in mammals of one or more clinical conditions selected from seizures, neurological disorders such as epilepsy and/or conditions in which there is neurological damage such as brain trauma, cerebral ischaemia, haemorrhage, head injuries and stroke.

A yet further aspect of the present invention provides a compound of formula I or a pharmaceutical composition containing a compound of formula I for use in the treatment, prophylaxis and/or inhibition of one or more clinical conditions selected from seizures, neurological disorders such as epilepsy and/or conditions in which there is neurological damage such as brain trauma, cerebral ischaemia, haemorrhage, head injuries and stroke in a mammal in need thereof.

Processes for the preparation of compounds of formula I will now be described. These processes form a further aspect of the present invention. The processes are preferably carried out at atmospheric pressure.

Compounds of formula I may be prepared by reacting compounds of formula III

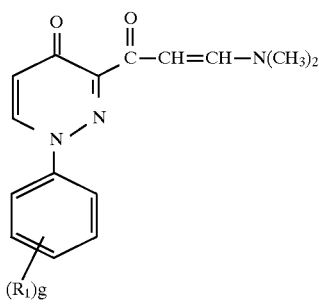

with compounds of formula IV

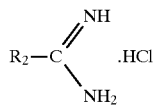 IV in the presence of a base, for example sodium ethoxide. Preferably, the reaction is carried out under an inert atmosphere, for example argon.

Compounds of formula 11 may be prepared in a similar manner to compounds of formula I Compounds of formula III may be prepared by heating compounds of formula V

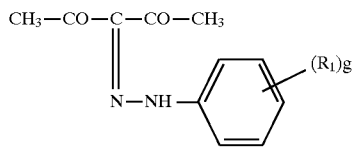 V with compounds of formula VI

 VI

Preferably, the reaction is carried out under an inert atmosphere, for example argon.

Compounds of formula IV, V and VI are commercially available or readily prepared by methods well known in the art.

The pharmacological activity of compounds of formula I or II was demonstrated by their activity in the following pharmacological tests.

The ability of the compounds to antagonise the myoclonic seizures induced in mice by the administration of bicuculline was observed. Hereinafter, this test is referred to as "BICM".

In the BICM experiments groups of female mice in the weight range 25 to 30 grammes had free access to food and water until one hour before administration of the compound to be tested. The compound to be tested was orally administered at one or more doses in 1% aqueous methylcellulose solution. One hour later (+)-bicuculline at a dose of 0.55 mg/kg was administered intravenously into a tail vein. Such a dose of (+)-bicuculline would generally be expected to induce a seizure in the mice.

During the following two minutes the animals were observed and the percentage of animals in which seizures had been inhibited was recorded. Thus, the greater the anticonvulsant activity of the compound, the higher was the percentage recorded in the BICM test.

A value for the dose inhibiting the seizures in 50% of the animals ($ED_{50}$) was calculated from the regression straight line plot of the percentage of animals in which seizures were inhibited against the dose of compound. The $ED_{50}$ values are presented in Table I The ability of the compounds to inhibit seizures in mice induced by a maximal electroshock was observed. Hereinafter, this test is referred to as 'MESM'.

In the MESM experiments, groups of male mice in the weight range 25 to 30 grammes had free access to food and water until the start of the experiment. The mice were divided into two groups, a control group and a test group to which a compound of formula I or II would be administered. The control group received an oral dose of 10 ml/kg of a vehicle of 1% aqueous methyl cellulose solution. The test group received orally, suspended in the same dose of the methylcellulose vehicle, a compound of formula I or II at a dose of either 100 mg/kg for initial testing or, if enough compound was available, at a range of doses to determine an $ED_{50}$ (see below). One hour after administration of all drugs an electroshock of duration 1.0 second was administered to all the mice in both groups through ear clip electrodes moistened with saline. The electrochock had an intensity of 99 mA, frequency of 50 Hz and pulse width of 0.4 ms. Such a shock would generally be expected to induce a seizure in the mice.

During the following two minutes the mice in each group were observed, the number of mice in each group exhibiting tonic hind limb extension was recorded and thus the percentage of mice in which seizures had been inhibited was determined. The greater the anticonvulsant activity of the compound of formula I or II, the higher was the percentage recorded in the MESM test.

If results at more than one dose were available, then a value for the dose inhibiting seizures in 50% of the mice ($ED_{50}$) was calculated from the regression straight line plot of the percentage of mice in which seizures were inhibited against the dose of the compound of formula I or II administered. The $ED_{50}$ values are presented in Table 1.

The compounds of formula I described hereinafter in the Examples have been found to have anticonvulsant activity in at least one of the BICM and/or MESM tests.

TABLE 1

| Example No. | BICM test* $ED_{50}$(mg/kg) | MESM test** $ED_{50}$(mg/kg) |
| --- | --- | --- |
| 1 | 4.7 | IA |
| 2 | 4.6 | 83.4 |
| 3 | IA | (50) |
| 4 | 157.5 | 73.6 |
| 5 | 11.8 | (50) |
| 6 | (60) | IA |
| 7 | (70) | IA |
| 8 | 12.9 | IA |
| 9 | IA | (50) |

*a figure in brackets indicates the % protection from bicuculline-induced seizures provided by a dose of 100 mg/kg (po) of the test compound.
**a figure in brackets indicates the % protection from MES-induced seizures provided by a dose of 100 mg/kg (po) of the test compound.
IA indicates that the compound did not achieve 50% protection from seizures in that test.

The invention will now be illustrated by the following non-limiting examples. The final product of each example was characterised using one or more of the following techniques: elemental analysis; infra-red spectroscopy; nuclear magnetic resonance spectroscopy; gas-liquid chromatography; and liquid chromatography. Temperatures are given in degrees Celsius.

EXAMPLE 1

3-(2-Tert-butylpyrimidin-4-yl)-1-(4-fluorophenyl) pyridazin-4(1H)-one is commercially available from the Maybridge Chemical Company, Tintagel, England under the number SPB 04026 on list 225.

Alternatively the compound may be prepared by condensing 2,2-dimethylpropanamidine with 3-1-(4-fluorophenyl)-4(1H)pyridazinone (which may be prepared by a similar method to that described in J. Het. Chem. 1981, 18, 333).

EXAMPLES 2–9

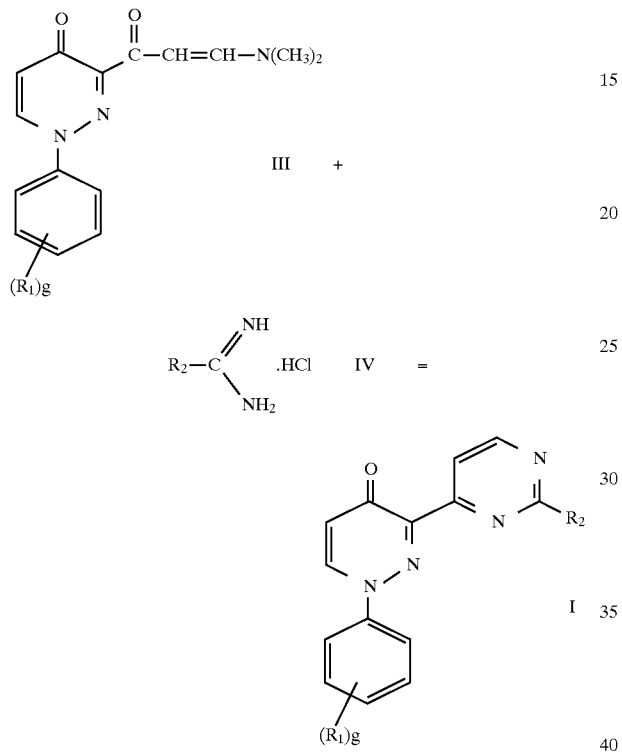

A compound of formula III (a grammes) and a compound of formula IV (b grammes) were added to a stirred solution of sodium (c grammes) in dry ethanol (d ml). The mixture was stirred under argon at room temperature for 3 days and solvent was removed under reduced pressure. The residue was purified by flash chromatography on silica gel using an e:f mixture of dichloromethane/ethanol as eluent to yield a compound of formula I (h grammes). A sample was recrystallised from solvent (i) to constant melting point.

$R_1$, g, $R_2$, a–f, h and i are defined in Table 2.

TABLE 2

| Ex. No | $R_1$ | g | $R_2$ | a | b | c | d | e | f | h | i | m.p. °C. | Notes |
|---|---|---|---|---|---|---|---|---|---|---|---|---|---|
| 2 | 4-F | 1 | i-propyl | 2.01 | 0.94 | 0.48 | 80 | 95 | 5 | 1.05 | ethyl acetate/n-hexane | 144–5 | |
| 3 | 4-F | 1 | phenyl | 3.02 | 2.20 | 0.72 | 100 | 98 | 2 | 1.07 | ethyl acetate/n-hexane | 145–7 | 1 |
| 4 | 2-Cl,4-Cl | 2 | H | 3.21 | 1.09 | 0.48 | 50 | 98 | 2 | 1.32 | toluene | 222–3 | 2,6 |
| 5 | 4-Cl | 1 | i-propyl | 6.08 | 2.70 | 1.40 | 250 | 9 | 1 | 2.95 | ethyl acetate | 141–2 | 1,4,7 |
| 6 | 4-Cl | 1 | cyclopropyl | 6.08 | 2.65 | 1.40 | 250 | 98 | 2 | 2.41 | ethyl acetate | 153–4 | 4 |
| 7 | 4-F | 1 | cyclohexyl | 6.10 | 3.75 | 1.45 | 250 | 98 | 2 | 1.23 | n-hexane | 124–5 | 5,8 |
| 8 | 4-Cl | 1 | cyclohexyl | 4.56 | 2.68 | 1.05 | 180 | 98 | 2 | 1.30 | ethyl acetate/n-hexane | 127–8 | 5,8 |
| 9 | 4-F | 1 | propyl | 7.65 | 4.24 | 1.61 | 175 | 98 | 2 | 3.19 | ethyl acetate | 145–6 | 3,1,4 |

Notes to Table 2
1. The mixture was stirred under argon for 4 days.
2. The compound of formula IV (acetate salt, not hydrochloride salt) was stirred for 15 minutes with sodium (c g) in ethanol (d ml) before adding the compound of formula III (a g) suspended in ethanol (50 ml). This mixture was heated under reflux for 2.5 hours. After cooling, the solvent was removed under reduced pressure, the residue was stirred with water (50 ml) and the solid was collected by filtration and purified by flash chromatography as per the standard procedure described above.
3. The compound of formula IV was stirred for 15 minutes with sodium (c g) in ethanol (d ml) before adding the compound of formula III (a g) as a solution in dry ethanol (100 ml).
4. The residue was stirred with water (100 ml) and the solid collected by filtration before flash chromatography.
5. The residue was washed with water (150 ml) and the product extracted with dichloromethane (2 × 150 ml). The organic layer was washed with water, dried over magnesium sulphate, and the solvent removed in vacuo to yield a solid which was purified by flash chromatography.
6. The eluent for flash chromatography was a mixture of chloroform/ethanol.
7. The eluent for flash chromatography was a mixture of petroleum ether (40–60° C.)/ethanol.
8. A second chromatography step was carried out using a 9:1 mixture of toluene/ethanol as eluent.

The compounds made by this procedure are named as follows:

| Ex. No. | Name |
| --- | --- |
| 2 | 3-(2-isopropylpyrimidin-4-yl)-1-(4-fluorophenyl)pyridazin-4(1H)-one |
| 3 | 3-(2-phenylpyrimidin-4-yl)-1-(4-fluorophenyl)pyridazin-4(1H)-one |
| 4 | 3-(pyrimidin-4-yl)-1-(2,4-dichlorophenyl)pyridazin-4(1H)-one |
| 5 | 3-(2-isopropylpyrimidin-4-yl)-1-(4-chlorophenyl)pyridazin-4(1H)-one |
| 6 | 3-(2-cyclopropyl pyrimidin-4-yl)-1-(4-chlorophenyl)pyridazin-4(1H)-one |
| 7 | 3-(2-cyclohexylpyrimidin-4-yl)-1-(4-fluorophenyl)pyridazin-4(1H)-one |
| 8 | 3-(2-cyclohexylpyrimidin-4-yl)-1-(4-chlorophenyl)pyridazin-4(1H)-one |
| 9 | 3-(2-propylpyrimidin-4-yl)-1-(4-fluorophenyl)pyridazin-4(1H)-one |

The compounds of formula IV are known in the art. The compounds of formula III were prepared as follows:

A. The Compound of Formula III in Which $R_1$ is 4-F, g is 1

A mixture of 3-(4-fluorophenylhydrazono)-2,4-pentanedione (8.00 g), and N,N-dimethyl-formamide dimethylacetal (18 ml) was heated under argon in an oil bath at 70° C. for 30 minutes.

Solvent was removed under reduced pressure and the residue purified by flash chromatography on silica gel using a 4:1 mixture of dichloromethane/ethanol as eluent, to afford 3-[3-(N,N-dimethylamino)-1-oxo-2-propenyl]1-(4-fluorophenyl)-4(1H)-pyridazi-none (9.46 g), m.p. (crude) 157°–8° C.

B. The Compound of Formula III in Which $R_1$ is 4-Cl, g is 1

A mixture of 3-(4-chlorophenylhydrazono)-2,4-pentanedione (15.20 g) and N,N-dimethyl formamide dimethylacetal (32 ml) was heated in an oil bath at 70° C. for 30 minutes.

Solvent was removed under reduced pressure and the residue purified by flash chromatography on silica gel using a 4:1 mixture of dichloromethane/ethanol as eluent, to afford 1-(4-chlorophenyl)-3-4(1H)-pyridazinone (17.16 g), m.p. (crude) 163–165° C.

C. The compound of formula III in which $R_1$ is 2-Cl, 4-Cl, g is 2

A mixture of 3-(2,4-dichlorophenylhydrazono)-2,4-pentanedione (4.20 g) and N,N-dimethylformamide dimethylacetal (20 ml) was heated in an oil bath at 120° C. for 5.5 hours.

Solvent was removed under reduced pressure and the residue purified by flash chromatography on silica gel using a 4:1 then 1:2 mixture of ethyl acetate/ethanol as eluent, to afford 2.33 g of 1,7-bis (N,N-dimethylamino)-1,6-heptadien-3,4,5-trione 4-(2,4-dichlorophenyl)hydrazone and 2.10 g of 1-(2,4-dichlorophenyl)-3-[3-(N,N-dimethylamino)-1-oxo-2-propenyl]4(1H)-pyridazinone.

1,7-bis(N,N-dimethylamino)-1,6-heptadien-3,4,5-trione 4-(2,4-dichlorophenyl)hydrazone (2.10 g) was dissolved in dry dichloromethane (6 ml), silica gel (19 g) was added and solvent was removed in vacuo. The mixture was heated at 80° C. for 30 minutes and then at 120° C. for 2 hours. After cooling, the product was extracted with acetone and the acetone was removed in vacuo. The oily residue was solidified with diethyl ether to afford 1-(2,4-dichlorophenyl)-3-[3-(N,N-dimethylamino)-1-oxo-2-propenyl]4(1H)-pyridazinone (1.40 g), m.p. 152°–154° C.

PHARMACEUTICAL EXAMPLES

Example U

In the preparation of capsules, 10 parts by weight of active compound and 240 parts by weight of lactose are de-aggregated and blended. The mixture is filled into hard gelatin capsules, each capsule containing 10 mg active compound.

Example V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tabletting machine to give tablets containing 10 mg of active compound.

Example W

Tablets are prepared by the method of the previous Example. The tablets are enteric coated in a conventional manner using a solution of 20% cellulose acetate phthalate and 3% diethyl phthalate in ethanol:dichloromethane (1:1).

Example X

In the preparation of suppositories, 100 parts by weight of active compound is incorporated in 1300 parts by weight of semi-synthetic glycerides as the suppository base and the mixture formed into suppositories each containing 100 mg of active ingredient.

Example Y

In the preparation of capsules, 50 parts by weight of active compound, 300 parts by weight of lactose and 3 parts by weight of magnesium stearate are deaggregated and blended. The mixture is filled into hard gelatin capsules, each capsule containing 50 mg of active ingredient.

Example Z

The active compound is incorporated into the base by thorough homogenization until the drug is evenly distributed. The ointment is packed into 10 g amber jars with screw-capped lined lids.

Active compound 0.1 g

White soft paraffin to 10 g

We claim:
1. Compounds of formula II

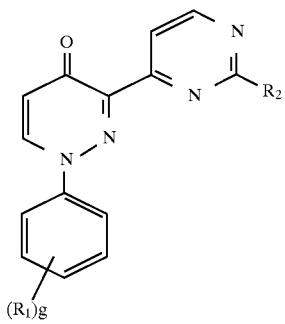

including pharmaceutically acceptable salts thereof; in which
g is 0,1,2,3,4 or 5;
$R_1$ independently represents halo; and
$R_2$ represents H, $C_{1-4}$ alkyl, $C_{3-6}$ cycloalkyl or phenyl optionally substituted by one or more substituents selected from halo, $C_{1-4}$ alkyl and $C_{1-4}$ alkoxy;
with the proviso that when g is 1 and $R_1$ is 4-fluoro, then $R_2$ is other than tert-butyl.

2. Compounds selected from:
3-(2-isopropylpyrimidin-4-yl)-1-(4-fluorophenyl)pyridazin-4(1H)-one;
3-(2-phenylpyrimidin-4-yl)-1-(4-fluorophenyl)pyridazin-4(1H)-one;
3-(pyrimidin-4-yl)-1-(2,4-dichlorophenyl)pyridazin-4(1H)-one;
3-(2-isopropylpyrimidin-4-yl)-1-(4-chlorophenyl)pyridazin-4(1H)-one;
3-(2-cyclopropylpyrimidin-4-yl)-1-(4-chlorophenyl)pyridazin-4(1H)-one;
3-(2-cyclohexylpyrimidin-4-yl)-1-(4-fluorophenyl)pyridazin-4(1H)-one;
3-(2-cyclohexylpyrimidin-4-yl)-1-(4-chlorophenyl)pyridazin-4(1H)-one; and
3-(2-propylpyrimidin-4-yl)-1-(4-fluorophenyl)pyridazin-4(1H)-one;
including pharmaceutically acceptable salts thereof.

3. A pharmaceutical composition comprising an effective amount of a compound of formula I

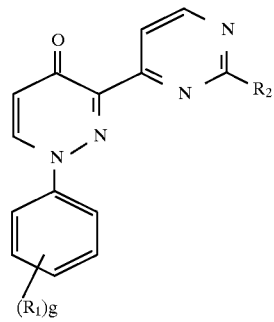

including pharmaceutically acceptable salts thereof; in which
g is 0,1,2,3,4 or 5;
$R_1$ independently represents halo; and
$R_2$ represents H, $C_{1-4}$ alkyl, $C_{3-6}$ cycloalkyl or phenyl optionally substituted by one or more substituents selected from halo, $C_{1-4}$ alkyl and $C_{1-4}$ alkoxy; in conjuction with a pharmaceutically acceptable diluent or carrier.

4. A pharmaceutical composition as claimed in claim 3 in which the compound of formula I is selected from:
3-(2-tert-butylpyrimidin-4-yl)-1-(4-fluorophenyl)pyridazin-4(1H)-one;
3-(2-isopropylpyrimidin-4-yl)-1-(4-fluorophenyl)pyridazin-4(1H)-one;
3-(2-phenylpyrimidin-4-yl)-1-(4-fluorophenyl)pyridazin-4(1H)-one;
3-(pyrimidin-4-yl)-1-(2,4-dichlorophenyl)pyridazin-4(1H)-one;
3-(2-isopropylpyrimidin-4-yl)-1-(4-chlorophenyl)pyridazin-4(1H)-one;
3-(2-cyclopropylpyrimidin-4-yl)-1-(4-chlorophenyl)pyridazin-4(1H)-one;
3-(2-cyclohexylpyrimidin-4-yl)-1-(4-fluorophenyl)pyridazin-4(1H)-one;
3-(2-cyclohexylpyrimidin-4-yl)-1-(4-chlorophenyl)pyridazin-4(1H)-one;
3-(2-propylpyrimidin-4-yl)-1-(4-fluorophenyl)pyridazin-4(1H)-one;

including pharmaceutically acceptable salts thereof.

5. A method of treatment, prophylaxis and/or inhibition of one or more clinical conditions selected from seizures, neurological disorders and/or conditions in which there is neurological damage, which comprises administering a therapeutically and/or prophylactically effective amount of a compound of formula I

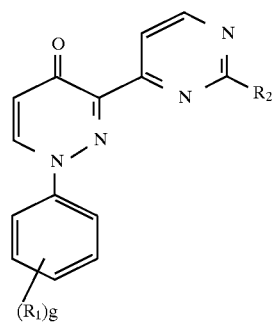

including pharmaceutically acceptable salts thereof; in which
g is 0,1,2,3,4 or 5;
$R_1$ independently represents halo; and
$R_2$ represents H, $C_{1-4}$ alkyl, $C_{3-6}$ cycloalkyl or phenyl optionally substituted by one or more substituents selected from halo, $C_{1-4}$ alkyl and $C_{1-4}$ alkoxy, to a mammal in need thereof.

6. A method of treatment, prophylaxis and/or inhibition as claimed in claim 5 in which the neurological disorder is epilepsy and the conditions in which there is neurological damage are brain trauma, cerebral ischaemia, haemorrhage, head injuries and stroke.

7. A process for the preparation of a compound of formula II as defined in claim 1, comprising the reaction of a compound of formula III

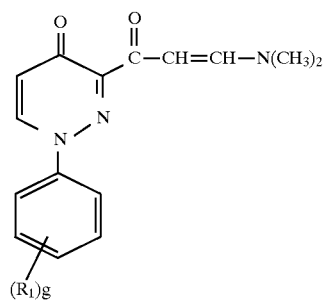
III
with a compound of formula IV
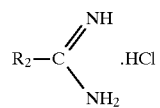
IV
in the presence of a base.
* * * * *